United States Patent
Banner et al.

(10) Patent No.: US 7,705,034 B2
(45) Date of Patent: Apr. 27, 2010

(54) VINYLOGOUS ACID DERIVATIVES

(75) Inventors: David Banner, Basel (CH); Hans Hilpert, Muenchenstein (CH); Bernd Kuhn, Liestal (CH); Harald Mauser, Schliengen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/903,579

(22) Filed: Sep. 24, 2007

(65) Prior Publication Data

US 2008/0096953 A1 Apr. 24, 2008

(30) Foreign Application Priority Data

Oct. 13, 2006 (EP) .................. 06122239

(51) Int. Cl.
- A61K 31/381 (2006.01)
- A61K 31/404 (2006.01)
- C07D 209/12 (2006.01)
- C07D 333/52 (2006.01)

(52) U.S. Cl. ............... 514/415; 514/443; 548/469; 549/58

(58) Field of Classification Search ............ 548/469; 549/58

See application file for complete search history.

(56) References Cited

U.S. PATENT DOCUMENTS

| | | | |
|---|---|---|---|
| 4,443,615 | A | 4/1984 | Matsuoka et al. |
| 5,814,631 | A | 9/1998 | Fukami et al. |
| 6,271,238 | B1 | 8/2001 | Suzuki et al. |
| 2003/0083315 | A1 | 5/2003 | Tsuchiya et al. |

FOREIGN PATENT DOCUMENTS

| | | |
|---|---|---|
| EP | 701 988 | 3/1996 |
| EP | 945 443 | 9/1999 |
| EP | 1 099 690 | 5/2001 |
| EP | 1 136 488 | 9/2001 |
| JP | 5078250 | 3/1993 |
| WO | WO 82/00032 | 2/1982 |
| WO | WO 88/00941 | 2/1988 |
| WO | WO 93/23040 | 11/1993 |
| WO | WO 93/23041 | 11/1993 |
| WO | WO 00/35452 | 6/2000 |
| WO | WO 2004/082687 | 9/2004 |

OTHER PUBLICATIONS

Hayashi, et al. Bioorg. Med. Chem. Lett. (2000), 10, pp. 199-201.*
Brand et al., Organic Letters, 5(13), pp. 2343-2346 (2003).
Kreighbaum et al., J. Med. Chem., 23(3), pp. 285-289 (1980).
Yang et al., Indian Journal of Chemistry, Section B: Organic Chemistry Including Medicinal Chemistry, 38B(8), pp. 897-904 (1999).
Hengartner et al., Journal of Organic Chemistry, 44(22), pp. 3741-3747 (1979).
Somei et al., Heterocycles, 33(1), pp. 77-80 (1992).
Tani et al., J. of Antibiotics, 57, pp. 89-96 (2004).
Pitlik, J. et al, *Bioorg. Med. Chem. Lett.* vol. 7, 3129-3134, (1997).
Adlington R.M. et al, *Bioog,. Med. Chem. Lett.* 7: 1689-1694, (1997).
Alcaide B. et al, *Tetrahedron* 61:7894-7906, (2005).
Aoyama, Y. et al, *Bioorg. Med. Chem. Lett* 10:2397-2401, (2000).
Aoyama, Y. et al, *Bioorg. Med. Chem.* 9:3065-3075, (2001).

* cited by examiner

*Primary Examiner*—Rebecca L Anderson
*Assistant Examiner*—Shawquia Young
(74) *Attorney, Agent, or Firm*—George W. Johnston; Dennis P. Tamaloni; Brian C. Remy

(57) ABSTRACT

The invention is concerned with novel vinylogous acid derivatives of formula I:

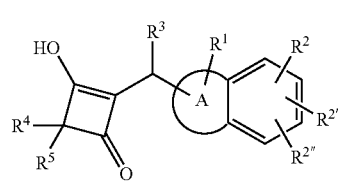

wherein A and $R^1$ to $R^5$ are as defined in the description and in the claims, as well as physiologically acceptable salts thereof. These compounds are useful as chymase inhibitors.

19 Claims, No Drawings

VINYLOGOUS ACID DERIVATIVES

PRIORITY TO RELATED APPLICATION(S)

This application claims the benefit of European Patent Application No. 06122239.4, filed Oct. 13, 2006, which is hereby incorporated by reference in its entirety.

BACKGROUND OF THE INVENTION

The invention relates to novel vinylogous acid derivatives of formula I, a process and an intermediate for the manufacture of such compounds, pharmaceutical compositions containing such compounds, and the use of such compounds. The compounds of formula I are useful as Chymase inhibitors.

Chymase is a serine proteinase with an expression pattern strictly limited to a sub-population of mast cells ($M_{CT}$ mast cell). Chymase is activated only upon mast cell activation and degranulation which restricts the enzyme activity to $M_{CT}$ positive tissues. Chymase is specifically cleaving a number of pathologically relevant substrates (Raymond, W. W., S. W. Ruggles, et al.; JBC 2003 278(36): 34517-34524) whereby it can activate Angiotensin II, Endothelin, TGFb, Il1, SCF, collagenase and degrade proteins like Thrombin, FN, APO A1,2. This pattern renders chymase an attractive target for allergic, inflammatory and fibrotic diseases. Indeed a number of successful animal studies with chymase inhibitors have demonstrated efficacy in atopic animals, vascular injury and atherosclerosis (Doggrell S A, Wanstall J C Can J Physiol Pharmacol. 2005 February; 83(2):123-30; Lindstedt K A, Kovanen P T. Curr Opin Lipidol. 2004 October; 15(5):567-73; Reed C E, Kita H. J Allergy Clin Immunol. 2004 November; 114(5):997-1008; Takai S, et al, Eur J. Pharmacol. 2004 Oct. 6; 501(1-3):1-8; Takai S, et al, Trends Pharmacol Sci. 2004 October; 25(10):518-22; Takai S, Miyazaki M. Curr Vasc Pharmacol. 2003 June; 1(2):217-24).

Thus inhibition of chymase appears a useful modality in Allergy, Asthma, peripheral arterial occlusive disease, critical limb ischemia, vulnerable atherosclerotic plaque patients, unstable angina, congestive heart failure, left ventricular hypertrophy, ischemia reperfusion injury, cardiomyopathy, restenosis, rheumatoid arthritis, diabetic nephropathy, irritable Bowel Disease, Crones disease, wound healing (burns/ulcers in Diabetes/CLI).

SUMMARY OF THE INVENTION

The present invention relates to the compounds of the formula I and all pharmaceutically acceptable salts thereof wherein formula I is:

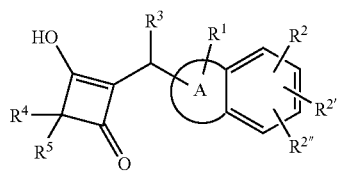

wherein $R^1$, $R^2$, $R^{2'}$, $R^{2''}$, $R^3$, $R^4$, and $R^5$, are as defined in the detailed description and in the claims. Compounds of formula I are useful as chymase inhibitors.

DETAILED DESCRIPTION OF THE INVENTION

Unless otherwise indicated, the following definitions are set forth to illustrate and define the meaning and scope of the various terms used to describe the invention herein.

The term "halogen" or "halo" means fluorine, chlorine, bromine or iodine. In preferred embodiments the halogen is chlorine or fluorine.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, iso-propyl, n-butyl, s-butyl, t-butyl. A $C_{1-4}$ alkyl is preferred.

The term "heteroalkyl" means a $C_{1-6}$ alkyl substituted by one or more substituents selected independently from the group consisting of nitro, hydroxy, halogen, cyano, $C_{1-6}$ alkoxy, formyl, $C_{1-6}$ alkylcarbonyl, carboxyl, $C_{1-6}$ alkylthio, $C_{1-6}$ alkyl sulfinyl, $C_{1-6}$ alkyl sulfonyl, amino and mono- or di-$C_{1-6}$ alkyl substituted amino. This term is further exemplified by such radicals as 2-hydroxyethyl and perfluoromethyl. A heteroalkyl wherein the $C_{1-6}$ alkyl is substituted by one hydroxy group or one to three of the same or different halogen atoms is preferred.

The term "$C_{3-7}$ cycloalkyl", alone or in combination with other groups, means a saturated monovalent cyclic hydrocarbon radical of three to seven ring carbons. Examples include cyclopropyl, cyclobutyl, and cyclohexyl.

The term "$C_{1-6}$ alkoxy", alone or in combination with other groups, means the group R'—O—, wherein R' is a $C_{1-6}$ alkyl.

The term "$C_{2-6}$ alkenyl", alone or in combination with other groups, means a straight-chain or branched hydrocarbon residue comprising an olefinic bond, having two to six carbon atoms. Examples include ethenyl and 2-propenyl.

The term "$C_{2-6}$-alkynyl", alone or in combination with other groups, means a straight-chain or branched hydrocarbon residue comprising a triple bond, having two to six carbon atoms. Examples include ethynyl and 2-propynyl.

The term "$C_{0-6}$ alkylene" means a bond if there are no carbon atoms, or a straight chain or branched divalent saturated aliphatic hydrocarbon group of 1 to 6 carbon atoms. $C_0$ alkylene means a bond.

The term "aryl", alone or in combination with other groups, means a phenyl or a naphthyl group. In preferred embodiments the aryl is a phenyl group.

The term "heterocyclyl", alone or in combination with other groups, means a non-aromatic monocyclic or bicyclic radical of three to eight ring atoms in which one or two ring atoms are heteroatoms selected from the group consisting of N, O, and $S(O)_n$ (where n is an integer from 0 to 2), with the remaining ring atoms being carbon.

The term "heteroaryl" means a monocyclic or bicyclic radical of 5 to 12 ring atoms having at least one aromatic ring containing one, two, or three ring heteroatoms selected from the group consisting of N, O, and S, with the remaining ring atoms being carbon. Preferably, the attachment point of the heteroaryl radical will be on an aromatic ring.

The term "optionally substituted aryl", "optionally substituted heteroaryl", "optionally substituted heterocyclyl" and "optionally substituted $C_{3-7}$ cycloalkyl" means, respectively aryl, heteroaryl, heterocyclyl and $C_{3-7}$ cycloalkyl optionally substituted by one or more substituents independently selected from the group consisting of halogen, nitro, cyano, amino, $C_{1-6}$ alkyl, $C_{2-6}$ alkenyl, $C_{2-6}$ alkynyl, hydroxy, $C_{1-6}$ alkoxy, mono- or di-$C_{1-6}$ alkyl substituted amino, and heteroalkyl.

In reference to a particular group or molecule, the term "substituted" refers to the fact that at least one of the hydrogen atoms of that group or molecule is replaced by some other substituent.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 300 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The terms "optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

The term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Unless otherwise indicated, the term "a compound of the formula" or "a compound of formula" or "compounds of the formula" or "compounds of formula" means any compound selected from the genus of compounds as defined by the formula.

In detail, the present invention relates to a compound of formula I:

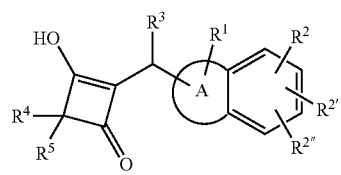

I or a pharmaceutically acceptable salt thereof, wherein:

A is selected from the group consisting of:
(1) a phenyl ring,
(2) a heteroaryl ring, which is a monocyclic aromatic ring of 5 or 6 ring atoms, containing one or two ring heteroatoms independently selected from the group consisting of N, O and S, with the remaining ring atoms being carbon,
(3) a heterocyclyl ring, which is a non-aromatic monocyclic ring of 5 or 6 ring atoms, containing one or two ring heteroatoms independently selected from the group consisting of N and $S(O)_n$, where n is an integer from 0 to 2, with the remaining ring atoms being carbon, wherein one of the ring carbon atoms of the heterocyclyl ring is optionally replaced with a carbonyl group;

$R^1$ is selected from the group consisting of:
(1) hydrogen,
(2) halogen,
(3) nitro,
(4) cyano,
(5) amino,
(6) $C_{1-6}$ alkyl,
(7) heteroalkyl,
(8) $C_{3-7}$ cycloalkyl,
(9) $C_{2-6}$ alkenyl,
(10) $C_{2-6}$ alkynyl,
(11) hydroxy,
(12) $C_{1-6}$ alkoxy,
(13) —NR'R", —($C_{0-6}$ alkylene)-NR'R", in which R' and R" are independently selected from the group consisting of:
 (a) hydrogen,
 (b) $C_{1-6}$ alkyl,
 (c) heteroalkyl,
 (d) formyl,
 (e) $C_{1-6}$ alkylcarbonyl,
 (f) optionally substituted $C_{3-7}$ cycloalkylcarbonyl,
 (g) optionally substituted arylcarbonyl,
 (h) optionally substituted heteroarylcarbonyl,
 (i) optionally substituted heterocyclylcarbonyl,
 (j) $C_{1-6}$ alkylsulfonyl,
 (k) optionally substituted $C_{3-7}$ cycloalkylsulfonyl,
 (l) optionally substituted arylsulfonyl,
 (m) optionally substituted heteroarylsulfonyl and
 (n) optionally substituted heterocyclylsulfonyl,
(14) —($C_{0-6}$ alkylene)-OR', in which R' is selected from the group consisting of hydrogen, $C_{1-6}$ alkyl, heteroalkyl, formyl and $C_{1-6}$ alkylcarbonyl;

$R^2$, $R^{2'}$ and $R^{2''}$ are independently selected from the group consisting of:
(1) hydrogen,
(2) halogen, (3) cyano,
(4) nitro,
(5) amino,
(6) mono- or di-$C_{1-6}$ alkyl substituted amino,
(7) $C_{1-6}$ alkyl,
(8) $C_{2-6}$ alkenyl,
(9) $C_{2-6}$ alkynyl,
(10) heteroalkyl,
(11) hydroxy, and
(12) $C_{1-6}$ alkoxy;

$R^3$ is selected from the group consisting of:
(1) hydrogen,
(2) halogen,
(3) cyano,
(4) nitro,
(5) amino,
(6) mono- or di-$C_{1-6}$ alkyl substituted amino,
(7) $C_{1-6}$ alkyl,
(8) $C_{2-6}$ alkenyl,
(9) $C_{2-6}$ alkynyl,
(10) heteroalkyl,
(11) hydroxy,
(12) $C_{1-6}$ alkoxy,
(13) optionally substituted $C_{3-7}$ cycloalkyl,
(14) optionally substituted aryl,
(15) optionally substituted heteroaryl,
(16) optionally substituted heterocyclyl,
(17) optionally substituted $C_{3-7}$ cycloalkyl $C_{1-6}$ alkyl,
(18) optionally substituted aryl $C_{1-6}$ alkyl,
(19) optionally substituted heteroaryl $C_{1-6}$ alkyl, and
(20) optionally substituted heterocyclyl $C_{1-6}$ alkyl;

$R^4$ and $R^5$, together with the carbon atom to which they are attached, form an optionally substituted $C_{3-7}$ cycloalkyl ring or an optionally substituted heterocyclyl ring; or alternatively, $R^5$ is hydrogen, halogen or $C_{1-6}$ alkyl, and $R^4$ is selected from the group consisting of:
(1) hydrogen,
(2) halogen,
(3) cyano,
(4) nitro,
(5) amino,
(6) mono- or di-$C_{1-6}$ alkyl substituted amino,
(7) $C_{1-6}$ alkyl,
(8) $C_{2-6}$ alkenyl,
(9) $C_{2-6}$ alkynyl,
(10) heteroalkyl,
(11) hydroxy,
(12) $C_{1-6}$ alkoxy,
(13) optionally substituted $C_{3-7}$ cycloalkyl,
(14) optionally substituted aryl,
(15) optionally substituted heteroaryl,
(16) optionally substituted heterocyclyl,
(17) optionally substituted $C_{3-7}$ cycloalkyl $C_{1-6}$ alkyl,
(18) optionally substituted aryl $C_{1-6}$ alkyl,
(19) optionally substituted heteroaryl $C_{1-6}$ alkyl, and
(20) optionally substituted heterocyclyl $C_{1-6}$ alkyl.

Preferred radicals for the chemical groups whose definitions are given above are those specifically exemplified in Examples.

Compounds of formula I can form pharmaceutically acceptable acid addition salts. Examples of such pharmaceutically acceptable salts are salts of compounds of formula I with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula I in which a COOH group is present can further form salts with bases. Examples of such salts are alkaline, earth-alkaline and ammonium salts such as e.g. Na—, K—, Ca— and Trimethylammoniumsalt. The term "pharmaceutically acceptable salts" also refers to such salts. Acid addition salts as described above are preferred.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula I can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, the compounds of formula I having certain radicals are preferred.

In the compounds of formula I,

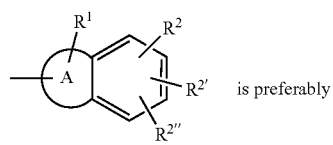 is preferably (a)

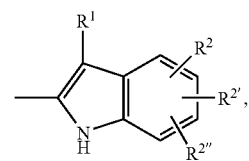 (a)

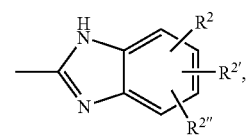 (b)

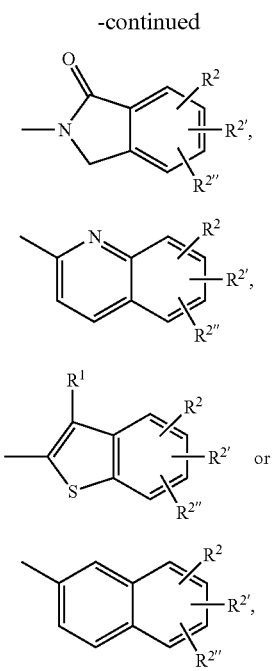

more preferably (a), (d), (e) or (f), further more preferably (a), (e) or (f), with (a) being especially preferred.

In the compounds of formula I, $R^3$ is preferably $C_{1-6}$ alkyl, optionally substituted aryl, optionally substituted heteroaryl, optionally substituted aryl $C_{1-6}$ alkyl or optionally substituted heteroaryl $C_{1-6}$ alkyl, more preferably $R^3$ is $C_{1-6}$ alkyl, phenyl optionally substituted by one to three fluorine atoms, heteroaryl optionally substituted by one to three fluorine atoms, in which heteroaryl is a monocyclic aromatic radical of 5 or 6 ring atoms, containing one or two ring nitrogen atoms or phenyl $C_{1-6}$ alkyl, and $R^3$ is especially phenyl.

In the compounds of formula I, $R^1$ is preferably hydrogen, $C_{1-6}$ alkyl, $C_{1-6}$ alkoxy, —($C_{0-6}$ alkylene)-NR'R", in which R' and R" are independently selected from the group consisting of hydrogen, formyl, $C_{1-6}$ alkylcarbonyl, optionally substituted arylcarbonyl, optionally substituted heteroarylcarbonyl, optionally substituted arylsulfonyl and optionally substituted heteroarylsulfonyl or —($C_{0-6}$ alkylene)-OR', in which R' is hydrogen or $C_{1-6}$ alkylcarbonyl. More preferably $R^1$ is $C_{1-6}$ alkyl, —($C_{2-6}$ alkylene)-NR'R", in which R' and R" are independently selected from the group consisting of hydrogen, formyl, acetyl, arylcarbonyl, in which aryl is optionally substituted by one or two perfluoro methyl and arylsulfonyl or —($C_{2-6}$ alkylene)-OR', in which R' is hydrogen or acetyl. More preferably $R^1$ is 2-aminoethyl, 2-acetylaminoethyl, 2-(N-formyl-N-methylamino)ethyl, 2-acetylamino-2,2-dimethylethyl, methyl, isopropyl or 2-hydroxyethyl. Especially preferred is where $R^1$ is methyl, 2-acetylaminoethyl, 2-acetylamino-2,2-dimethylethyl or 2-(N-formyl-N-methylamino)ethyl.

In the compounds of formula I, $R^2$, $R^{2'}$ and $R^{2''}$ are preferably independently from each other hydrogen, halogen, $C_{1-6}$ alkyl or $C_{1-6}$ alkoxy. More preferably two of $R^2$, $R^{2'}$ and $R^{2''}$ are hydrogen, and the other is hydrogen, halogen, $C_{1-6}$ alkyl or $C_{1-6}$ alkoxy. More preferably two of $R^2$, $R^{2'}$ and $R^{2''}$ are hydrogen, and the other is hydrogen, chloro, fluoro, methyl, ethyl or methoxy. Especially two of $R^2$, $R^{2'}$ and $R^{2''}$ are hydrogen, and the other is hydrogen, fluoro or methyl.

In the compounds of formula I, $R^4$ is preferably hydrogen, $C_{1-6}$ alkyl, optionally substituted $C_{3-7}$ cycloalkyl, optionally substituted aryl, optionally substituted $C_{3-7}$ cycloalkyl $C_{1-6}$ alkyl or optionally substituted aryl $C_{1-6}$ alkyl; or $R^4$ and $R^5$, together with the carbon atom to which they are attached, form optionally substituted $C_{3-7}$ cycloalkyl ring. More preferably $R^4$ is $C_{1-6}$ alkyl, optionally substituted aryl or optionally substituted aryl $C_{1-6}$ alkyl, and $R^5$ is halogen or $C_{1-6}$ alkyl. Especially $R^4$ is phenyl or 4-methylphenyl, and $R^5$ is methyl.

Preferred compound of the invention is a compound of formula I, which is

N-(2-{2-[(2-Hydroxy-3-methyl-4-oxo-3-phenyl-cyclobut-1-enyl)-phenyl-methyl]-6-methyl-1H-indol-3-yl}-1,1-dimethyl-ethyl)-acetamide, 3-Hydroxy-4-methyl-2-[(3-methyl-1H-indol-2-yl)-phenyl-methyl]-4-phenyl-cyclobut-2-enone, 2-[(3,5-Dimethyl-1H-indol-2-yl)-phenyl-methyl]-3-hydroxy-4-methyl-4-phenyl-cyclobut-2-enone, 2-[(3,6-Dimethyl-1H-indol-2-yl)-phenyl-methyl]-3-hydroxy-4-methyl-4-phenyl-cyclobut-2-enone, 2-[(5-Fluoro-3-methyl-1H-indol-2-yl)-phenyl-methyl]-3-hydroxy-4-methyl-4-phenyl-cyclobut-2-enone, N-{2-[(2-Hydroxy-3-methyl-4-oxo-3-phenyl-cyclobut-1-enyl)-phenyl-methyl]-6-methyl-1H-indol-3-ylmethyl}-acetamide, 3-Hydroxy-4-methyl-2-[(3-methyl-1H-indol-2-yl)-phenyl-methyl]-4-p-tolyl-cyclobut-2-enone, 2-[(3,5-Dimethyl-1H-indol-2-yl)-phenyl-methyl]-3-hydroxy-4-methyl-4-p-tolyl-cyclobut-2-enone, 2-[(3,6-Dimethyl-1H-indol-2-yl)-phenyl-methyl]-3-hydroxy-4-methyl-4-p-tolyl-cyclobut-2-enone, 2-[(5-Fluoro-3-methyl-1H-indol-2-yl)-phenyl-methyl]-3-hydroxy-4-methyl-4-p-tolyl-cyclobut-2-enone, N-{2-[(2-Hydroxy-3-methyl-4-oxo-3-p-tolyl-cyclobut-1-enyl)-phenyl-methyl]-6-methyl-1H-indol-3-ylmethyl}-acetamide or N-{2-[(2-Hydroxy-3-methyl-4-oxo-3-p-tolyl-cyclobut-1-enyl)-phenyl-methyl]-6-methyl-1H-indol-3-ylmethyl}-N-methyl-formamide.

The compounds of the present invention can be prepared, for example, by the general synthetic procedures described below.

General Synthetic Procedures

I) The compounds of formula I, wherein

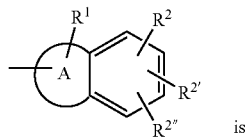

is

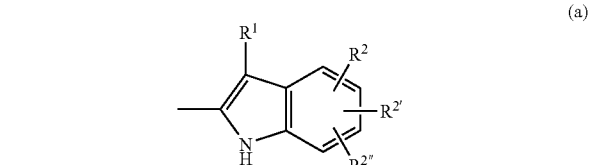

in which $R^1$, $R^2$, $R^{2'}$ and $R^{2''}$ are as defined before) can be prepared in accordance with the following scheme 1:

Scheme 1

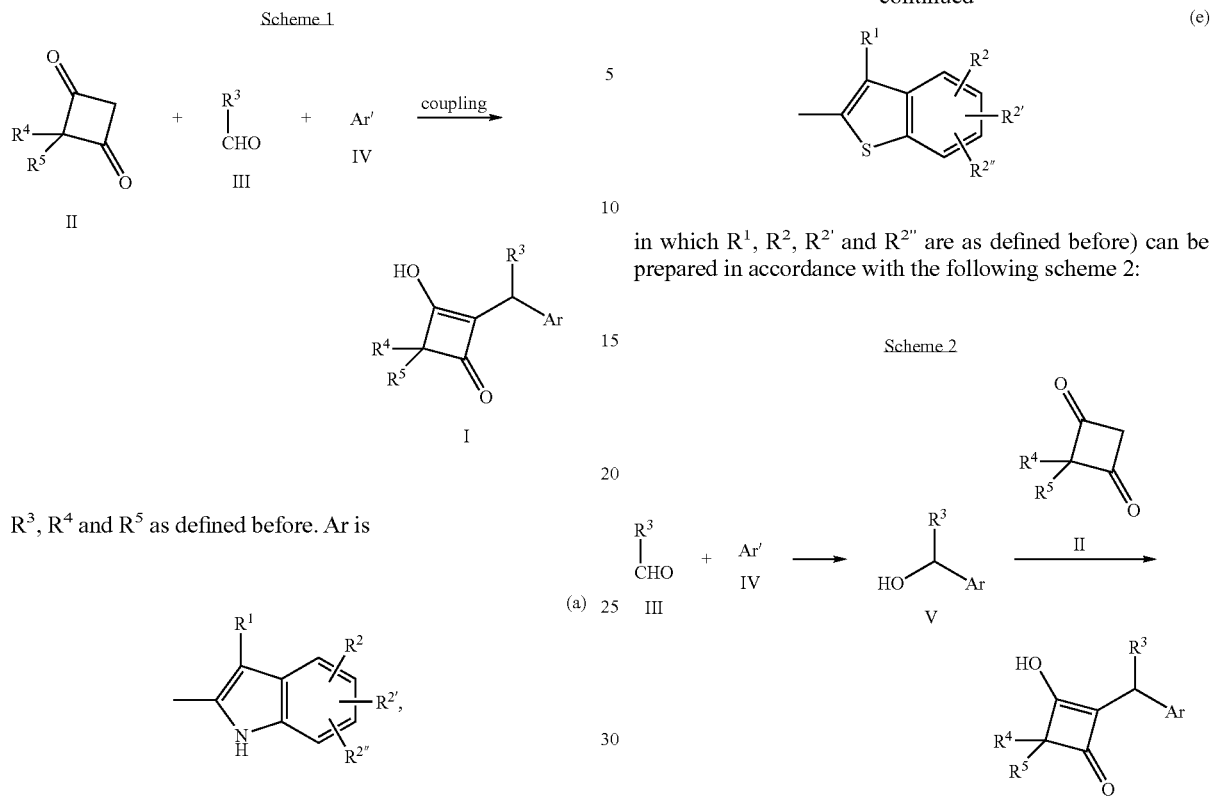

R³, R⁴ and R⁵ as defined before. Ar is (a)

and Ar' is wherein R¹, R², R²' and R²'' are as defined before.

The coupling of a diketone II (exists as an equilibrium of the keto and enol form), an aldehyde III and an aromatic compound IV to the vinylogous acid I can be effected in a solvent such as CH₃CN or an acid such as a carbonic acid, e.g. formic acid or preferably acetic acid at a temperature in the range of 22° C.-100° C., preferably at 22° C. for 1-20 h.

II) The compounds of formula I, wherein is (f)

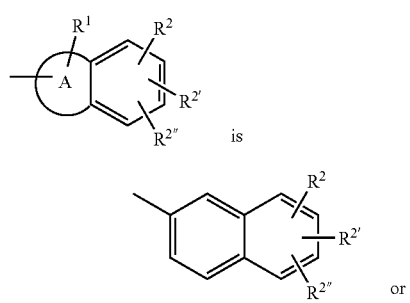

or (e)

in which R¹, R², R²' and R²'' are as defined before) can be prepared in accordance with the following scheme 2:

Scheme 2

R³, R⁴ and R⁵ are as defined before. Ar is (f)

or (e)

and Ar' is

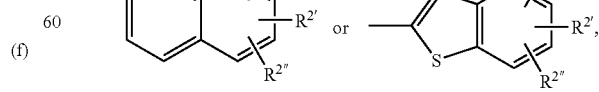

wherein R¹, R², R²' and R²'' are as defined before.

An aromatic compound Ar IV such as 2-halogen substituted naphthyl derivatives or benzothiophene derivatives can be lithiated at position 2 with an alkyl lithium reagent such as n-butyl lithium in a solvent like e.g. ethyl ether or preferably tetrahydrofurane at −100° C. to 60° C., preferably at −80° C. The lithiated intermediate obtained can be reacted with an aldehyde III at −80° C. to 22° C. to give the alcohol V.

The alcohol V may be reacted with the diketone II in the presence of a carbonic acid, e.g. acetic acid or preferably trifluoroacetic acid in a solvent such as an ether or preferably dichloromethane at a temperature in the range of 22° C.-50° C., preferably at 22° C. for 1-20 h to afford the vinylogous acid I.

III) The starting materials of formula II may be prepared in accordance with the following scheme 3:

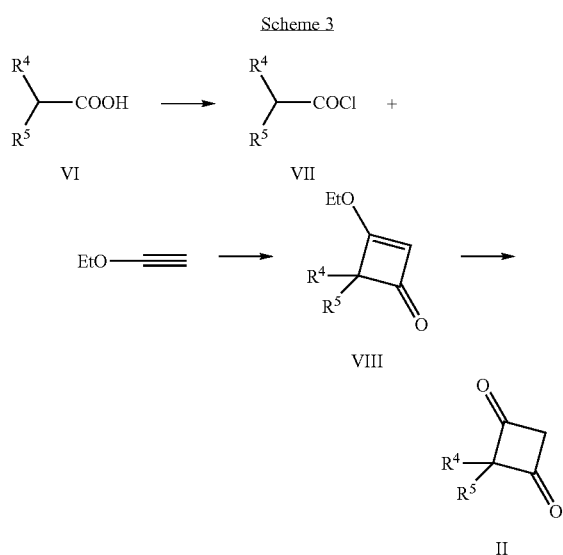

Scheme 3 wherein $R^4$ and $R^5$ are as defined before.

An acid VI may be converted to an acid chloride by standard methods using oxalyl chloride or preferably thionylchloride to give the acid chloride VII. The acid chloride can be reacted with ethoxy acetylene in the presence of a base, such as an alkyl amine, preferably triethylamine in a solvent like an ether, preferably diethyl ether at 0° C.-40° C., preferably at 40° C. to give the ethylester VIII. Hydrolysis of the ethylester VIII can be effected with a strong mineral acid, preferably hydrochloric acid in a solvent such as an ether, preferably tetrahydrofurane at 0° C.-60° C., preferably at 22° C. to give the diketone II.

The starting material of formula II can be prepared according to the following literature reference:

1) Brand, Stephen et al., Organic Letters (2003), 5(13), 2343-2346.

IV) The starting materials of formula III are all commercially available.

V) Most of the aromatic compounds of formula IV are commercially available, or can be prepared by a skilled person, using his/her common general knowledge. The compounds of formula IV can also be prepared, according to the following literature references:

2) Kreighbaum, William E. et al., J. Med. Chem. (1980), 23(3), 285-9.

3) Yang, Shyh-Chyun et al., Indian Journal of Chemistry, Section B: Organic Chemistry Including Medicinal Chemistry (1999), 38B(8), 897-904.

4) Tsuchiya, Michihiro et al., international patent application, WO8200032 (1982).

5) Hengartner, Urs et al., Journal of Organic Chemistry (1979), 44(22), 3741-7.

6) Somei, Masanori et al., Heterocycles (1992), 33(1), 77-80.

VI) The starting materials of formula VI are all commercially available.

As described above, the compounds of formula I are active compounds and inhibit chymase. These compounds consequently prevent the activation of Angiotensin II, Endothelin, TGFb, Il1, SCF, collagenase and degradation of proteins like Thrombin, FN, APO A1,2. They therefore can be used for the treatment and/or prevention of allergic, inflammatory and/or fibrotic diseases, such as allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, atherothrombosis and/or burns/ulcers in Diabetes/CLI.

Prevention and/or treatment of allergic, inflammatory or fibrotic diseases, particularly atherothrombosis or asthma, is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of allergic, inflammatory and/or fibrotic diseases, particularly as therapeutically active substances for the treatment and/or prophylaxis of allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, atherothrombosis and/or burns/ulcers in Diabetes/CLI.

The invention also relates to the use of compounds as described above for the preparation of medicaments for the therapeutic and/or prophylactic treatment of allergic, inflammatory and/or fibrotic diseases, particularly for the therapeutic and/or prophylactic treatment of allergy, asthma, peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, atherothrombosis and/or burns/ulcers in Diabetes/CLI. Such medicaments comprise a compound as described above.

The invention also relates to the process and the intermediates for manufacturing the compounds of formula I as well as the process for manufacturing the intermediates.

The inhibition of chymase by the compounds of the present invention can be demonstrated by the peptide substrate assay as described hereinafter.

For the chymase a substrate was chosen containing the 4 amino acid peptide AAPF as a standard substrate for chymotrypsin like compounds (succinyl-Ala-Ala-Pro-Phe-[7-amino-4-methylcoumarin]; Lockhart B E, et al., "Recombinant human mast-cell chymase: an improved procedure for expression in *Pichia pastoris* and purification of the highly active enzyme." *Biotechnol Appl Biochem.* published as immediate publication 26 May 2004 as manuscript BA20040074)). The peptide was synthesized with a purity of 95% from Bachem, Bubendorf, Switzerland). Chymase purified form human skin mast cells was obtained from Calbiochem (Merck Biosciences, San Diego, Calif., USA). The assay buffer was 0.15 M NaCl, 0.05M, Tris HCl, 0.05% CHAPS (3-[(3-Cholamidopropyl)-dimethylammonio]-1-propane sulphonate), 0.1 mg/ml Heparin (Heparin sodium, Sigma, porcine intestinal mucosa), 0.02 mM AAPF-substrate, 1 nM Chymase at pH 7.4. The assay was performed in 96-well plates (Packard Optiplate), with a 0.05 ml volume at room temperature. Chymase activity was indicated by the initial rate of increase in fluorescence at 340/440 nm (excitation/emission) from free 7-amino-4-methylcoumarin released from the substrate. Inhibition of the activity by inhibitory compounds was read after 30 min pre-incubation with the chymase at room temperature in assay buffer without AAPF-substrate. The assay was then started by addition of the indicated concentration of AAPF-substrate.

The IC50 values of the active compounds of the present invention preferably amount to about 1000 to 1 nM, especially about 50 to 1 nM.

| Example | IC50(nM) |
|---------|----------|
| Example 3 | 27 |
| Example 6 | 34 |
| Example 10 | 25 |
| Example 13 | 8 |

The compounds of formula I and/or their pharmaceutically acceptable salts can be used as medicaments, e.g. in the form of pharmaceutical compositions for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula I.

EXAMPLES

The following Examples serve to illustrate the present invention in more detail. They are, however, not intended to limit its scope in any manner.

General Procedure A: Preparation of the Diketone II

A1. A mixture of the acid VI (30 mmole) in toluene (10 ml) was treated with thionyl chloride (90 mmole) and heated to reflux for ca. 1 h until gas evolution ceased. The mixture was evaporated to dryness to give the acid chloride VII which was used without further purification.

A2. To a stirred solution of the acid chloride VII (30 mmole) and ethoxy acetylene (40% in hexane, 60 mmole) in diethyl ether (70 ml) was added at 22° C. triethylamine (50 mmole) and stirring was continued at reflux temperature for 20 h. The suspension was filtered, the filtrate evaporated and the residue chromatographed on silica to give the ethylester VIII.

A3. A mixture of the ethylester VIII (2 mmole) and aqueous hydrochloric acid (25%, 1.5 ml) in tetrahydrofurane (2 ml) was stirred at 22° C. for 16 h. The mixture was evaporated and the residue partitioned between aqueous hydrochloric acid (1 N) and ethyl acetate. The organic layer was dried evaporated and chromatographed on silica to give the diketone II.

General Procedure B: Preparation of the Alcohols V

To a solution of a 2-bromonaphthalene derivative (10 mmole) or a benzothiophene derivative (10 mmole) in tetrahydrofurane (150 ml) was added at −78° C. n-butyllithium (1.6 M in n-hexane, 11 mmole) and stirring was continued at −78° C. for 1 h (in case of the benzothiophene derivatives stirring was continued at 22° C. followed by cooling to −78° C.). The mixture was treated with a solution of the aldehyde III (10 mmole) in tetrahydrofurane (20 ml) and stirring was continued for 30 min. The mixture was quenched with saturated aqueous $NH_4Cl$ and extracted with ethyl acetate. The organic layer was dried evaporated and the residue chromatographed on silica to give the alcohols V.

General Procedure C: Coupling of a Diketone II an Aldehyde III and an Aromatic Compound Such as an Indole IV A solution of the diketone II (1 mmole), the aldehyde III (1.3 mmole) and the indole IV (1 mmole) in acetic acid (4 ml) was stirred at 22° C. for 16 h. The suspension was filtered and the residue washed with pentane. If no precipitations occurred, the solution was purified on preparative HPLC(RP-18, CH$_3$CN/H$_2$O, gradient) to give the vinylogous acids I.

General Procedure D: Coupling of a Diketone II and an Alcohol V

A solution of the diketone II (0.2 mmole) and the alcohol V (0.2 mmole) in dichloromethane (2 ml) was added trifluoroacetic acid (0.4 mmole) and stirring was continued at 22° C. for 6 h. The suspension was evaporated and the residue washed with n-pentane. If no precipitation occurred, the solution was purified on preparative HPLC(RP-18, CH$_3$CN/H$_2$O, gradient) to give the vinylogous acids I.

Example 1

N-(2-{2-[(2-Hydroxy-3-isobutyl-3-methyl-4-oxo-cyclobut-1-enyl)-phenyl-methyl]-6-methyl-1H-indol-3-yl}-1,1-dimethyl-ethyl)-acetamide

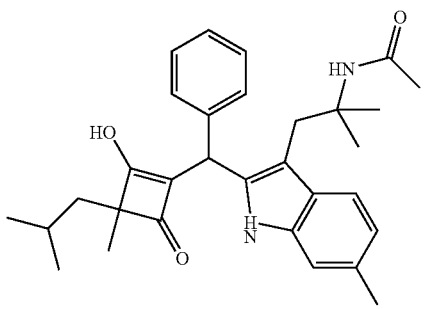

1.1. Using general procedure A, 2,4-dimethyl-pentanoic acid was converted to 2-isobutyl-2-methyl-cyclobutane-1,3-dione, obtained as a brown oil. MS: 153.4 ([M–H]$^-$).

1.2. A solution of 1,1-dimethyl-2-(6-methyl-1H-indol-3-yl)-ethylamine (2 mmole, prepared according to Lit. 2) and acetic anhydride (2.2 mmole) in dichloromethane (3 ml) was treated with triethylamine (6 mmole) and the mixture was stirred at 22° C. for 18 h. The mixture was washed with aqueous hydrochloric acid (1N), the organic layer was dried and evaporated to give N-[1,1-dimethyl-2-(6-methyl-1H-indol-3-yl)-ethyl]-acetamide as a brownish solid. MS: 243.2 ([M–H]$^-$).

1.3. Using general procedure C, 2-isobutyl-2-methyl-cyclobutane-1,3-dione was reacted with benzaldehyde and N-[1,1-dimethyl-2-(6-methyl-1H-indol-3-yl)-ethyl]-acetamide to give N-(2-{2-[(2-hydroxy-3-isobutyl-3-methyl-4-oxo-cyclobut-1-enyl)-phenyl-methyl]-6-methyl-1H-indol-3-yl}-1,1-dimethyl-ethyl)-acetamide as a pale brown solid. MS: 485.6 ([M–H]$^-$).

Example 2

N-(2-{2-[(3-Benzyl-2-hydroxy-3-methyl-4-oxo-cyclobut-1-enyl)-phenyl-methyl]-6-methyl-1H-indol-3-yl}-1,1-dimethyl-ethyl)-acetamide

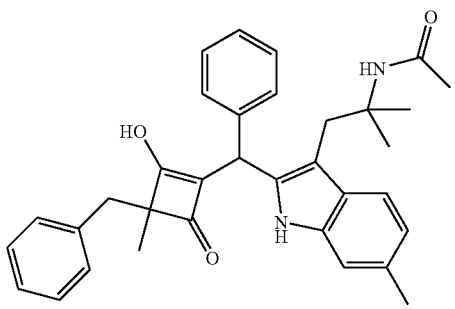

Using general procedure C, 2-benzyl-2-methyl-cyclobutane-1,3-dione (Lit. 1) was reacted with benzaldehyde and N-[1,1-dimethyl-2-(6-methyl-1H-indol-3-yl)-ethyl]-acetamide (from Example 1.2) to give the title compound as a red solid. MS: 519.5 ([M–H]$^-$).

Example 3

N-(2-{2-[(2-Hydroxy-3-methyl-4-oxo-3-phenyl-cyclobut-1-enyl)-phenyl-methyl]-6-methyl-1H-indol-3-yl}-1,1-dimethyl-ethyl)-acetamide

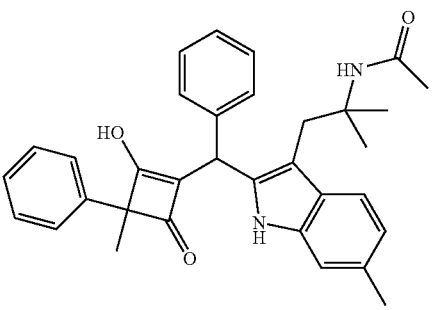

Using general procedure C, 2-methyl-2-phenyl-cyclobutane-1,3-dione (Lit. 1) was reacted with benzaldehyde and N-[1,1-dimethyl-2-(6-methyl-1H-indol-3-yl)-ethyl]-acetamide (from Example 1.2) to give the title compound as a pale yellow solid. MS: 505.5 ([M–H]$^-$).

Example 4

N-(2-{2-[(2-Hydroxy-3-methyl-4-oxo-3-p-tolyl-cyclobut-1-enyl)-phenyl-methyl]-6-methyl-1H-indol-3-yl}-1,1-dimethyl-ethyl)-acetamide

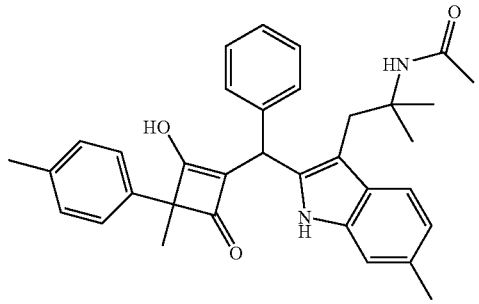

4.1. Using general procedure A, 2-p-tolyl-propionic acid was converted to 2-methyl-2-p-tolyl-cyclobutane-1,3-dione, obtained as a brown oil. MS: 187.4 ([M–H]$^-$).

4.2. Using general procedure C, 2-methyl-2-p-tolyl-cyclobutane-1,3-dione was reacted with benzaldehyde and N-[1,1-dimethyl-2-(6-methyl-1H-indol-3-yl)-ethyl]-acetamide (from Example 1.2) to give N-(2-{2-[(2-hydroxy-3-methyl-4-oxo-3-p-tolyl-cyclobut-1-enyl)-phenyl-methyl]-6-methyl-1H-indol-3-yl}-1,1-dimethyl-ethyl)-acetamide as a pale yellow solid. MS: 519.5 ([M–H]$^-$).

Example 5

N-[2-(2-{[3-(4-Chloro-phenyl)-2-hydroxy-3-methyl-4-oxo-cyclobut-1-enyl]-phenyl-methyl}-6-methyl-1H-indol-3-yl)-1,1-dimethyl-ethyl]-acetamide

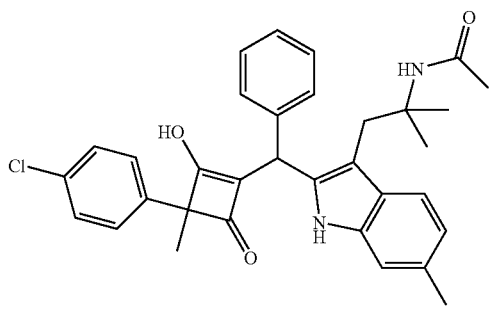

5.1. Using general procedure A, 2-(4-chloro-phenyl)-propionic acid was converted to 2-(4-chloro-phenyl)-2-methyl-cyclobutane-1,3-dione, obtained as a brown oil. MS: 206.9 ([M–H]–).

5.2. Using general procedure C, 2-(4-chloro-phenyl)-2-methyl-cyclobutane-1,3-dione was reacted with benzaldehyde and N-[1,1-dimethyl-2-(6-methyl-1H-indol-3-yl)-ethyl]-acetamide (from Example 1.2) to give N-[2-(2-{[3-(4-chloro-phenyl)-2-hydroxy-3-methyl-4-oxo-cyclobut-1-enyl]-phenyl-methyl}-6-methyl-1H-indol-3-yl)-1,1-dimethyl-ethyl]-acetamide as a pale yellow solid. MS: 539.5 ([M–H]$^-$).

Example 6

3-Hydroxy-4-methyl-2-[(3-methyl-1H-indol-2-yl)-phenyl-methyl]-4-phenyl-cyclobut-2-enone

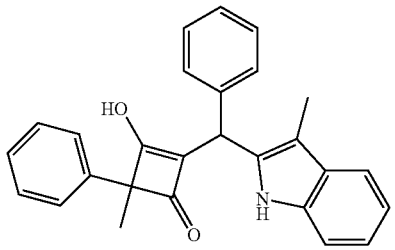

Using general procedure C, 2-methyl-2-phenyl-cyclobutane-1,3-dione (Lit. 1) was reacted with benzaldehyde and 3-methyl-1H-indole to give the title compound as a colorless solid. MS: 392.3 ([M–H]$^-$).

Example 7

2-[(3,5-Dimethyl-1H-indol-2-yl)-phenyl-methyl]-3-hydroxy-4-methyl-4-phenyl-cyclobut-2-enone

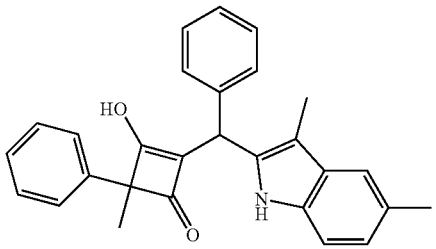

Using general procedure C, 2-methyl-2-phenyl-cyclobutane-1,3-dione (Lit. 1) was reacted with benzaldehyde and 3,5-dimethyl-1H-indole (Lit. 3) to give the title compound as a colorless solid. MS: 406.5 ([M–H]$^-$).

Example 8

2-[(3,6-Dimethyl-1H-indol-2-yl)-phenyl-methyl]-3-hydroxy-4-methyl-4-phenyl-cyclobut-2-enone

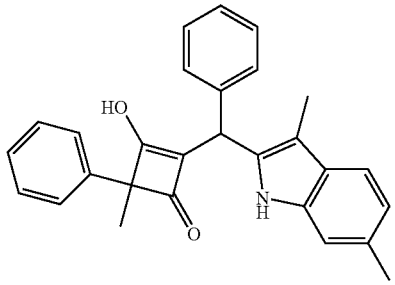

Using general procedure C, 2-methyl-2-phenyl-cyclobutane-1,3-dione (Lit. 1) was reacted with benzaldehyde and 3,6-dimethyl-1H-indole (Lit. 4) to give the title compound as a colorless solid. MS: 406.4 ([M–H]$^-$).

Example 9

2-[(5-Fluoro-3-methyl-1H-indol-2-yl)-phenyl-methyl]-3-hydroxy-4-methyl-4-phenyl-cyclobut-2-enone

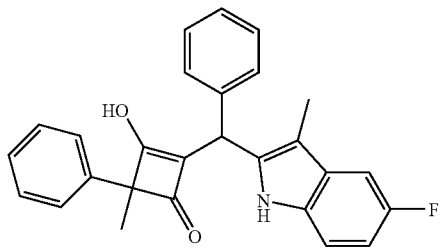

Using general procedure C, 2-methyl-2-phenyl-cyclobutane-1,3-dione (Lit. 1) was reacted with benzaldehyde and 5-fluoro-3-methyl-1H-indole to give the title compound as a colorless solid. MS: 410.3 ([M−H]⁻).

Example 10

N-{2-[(2-Hydroxy-3-methyl-4-oxo-3-phenyl-cyclobut-1-enyl)-phenyl-methyl]-6-methyl-1H-indol-3-ylmethyl}-acetamide 10.1. To a solution of 6-methyl-1H-indole-3-carbaldehyde (0.96 g, Lit. 5) in ethanol (30 ml) was added at 22° C. hydroxylamine hydrochloride (0.46 g) and sodium acetate (0.54 g) and the mixture was stirred for 3 h. The mixture was evaporated and the residue triturated with water and dichloromethane/n-heptane (1:1) and dried to give 6-methyl-1H-indole-3-carbaldehyde oxime (0.96 g) as a pink solid. MS: 175.3 ([M+H]+).

10.2. To a mixture of 6-methyl-1H-indole-3-carbaldehyde oxime (0.66 g) and NiCl₂.6H₂O (0.97 g) in methanol (60 ml) was added at 22° C. sodium borohydride (3.04 g) in portions. The suspension was filtered and the filtrate evaporated. The residue was partitioned between aqueous NH3 (1%) and ethyl acetate, the organic layer was dried and evaporated to the give crude C-(6-methyl-1H-indol-3-yl)-methylamine as a yellow semi solid (0.68 g).

10.3. To a solution of C-(6-methyl-1H-indol-3-yl)-methylamine (0.24 g) in dichloromethane (4 ml) was added acetic anhydride (0.14 ml) and pyridine (0.13 ml) and stirring was continued at 22° C. for 20 min. The mixture was washed with aqueous HCl (1N), the organic layer was dried and evaporated. The residue was chromatographed on silica using dichloromethane/methanol (70:1) to give N-(6-methyl-1H-indol-3-ylmethyl)-acetamide as colorless foam (0.15 g). MS: 203.1 ([M+H]+).

10.4. Using general procedure C, 2-methyl-2-phenyl-cyclobutane-1,3-dione (Lit. 1) was reacted with benzaldehyde and N-(6-methyl-1H-indol-3-ylmethyl)-acetamide to give N-{2-[(2-hydroxy-3-methyl-4-oxo-3-phenyl-cyclobut-1-enyl)-phenyl-methyl]-6-methyl-1H-indol-3-ylmethyl}-acetamide as a pale red solid. MS: 463.4 ([M−H]⁻).

Example 11

3-Hydroxy-4-methyl-2-[(3-methyl-1H-indol-2-yl)-phenyl-methyl]-4-p-tolyl-cyclobut-2-enone

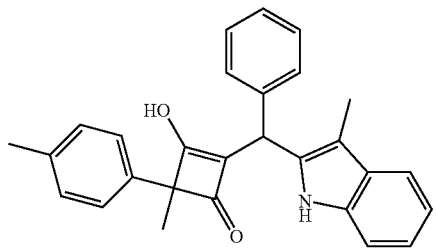

Using general procedure C, 2-methyl-2-p-tolyl-cyclobutane-1,3-dione (from Example 4.1) was reacted with benzaldehyde and 3-methyl-1H-indole to give the title compound as a colorless solid. MS: 406.6 ([M−H]⁻).

Example 12

2-[(3,5-Dimethyl-1H-indol-2-yl)-phenyl-methyl]-3-hydroxy-4-methyl-4-p-tolyl-cyclobut-2-enone

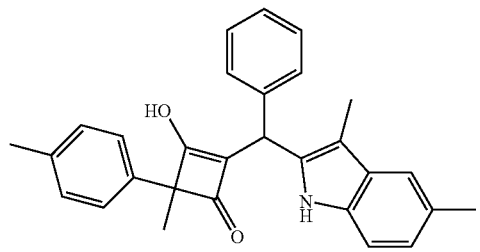

Using general procedure C, 2-methyl-2-p-tolyl-cyclobutane-1,3-dione (from Example 4.1) was reacted with benzaldehyde and 3,5-dimethyl-1H-indole (Lit. 3) to give the title compound as a colorless solid. MS: 420.5 ([M−H]⁻).

Example 13

2-[(3,6-Dimethyl-1H-indol-2-yl)-phenyl-methyl]-3-hydroxy-4-methyl-4-p-tolyl-cyclobut-2-enone

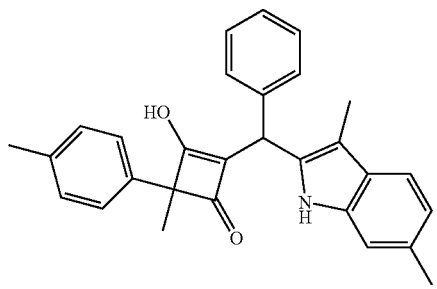

Using general procedure C, 2-methyl-2-p-tolyl-cyclobutane-1,3-dione (from Example 4.1) was reacted with benzaldehyde and 3,6-dimethyl-1H-indole (Lit. 4) to give the title compound as a colorless solid. MS: 420.5 ([M−H]⁻).

Example 14

2-[(5-Fluoro-3-methyl-1H-indol-2-yl)-phenyl-methyl]-3-hydroxy-4-methyl-4-p-tolyl-cyclobut-2-enone

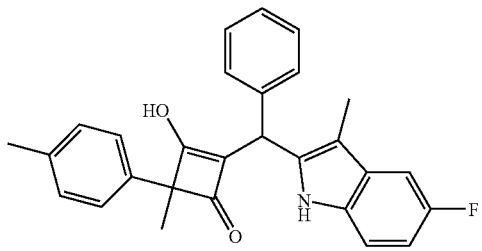

Using general procedure C, 2-methyl-2-p-tolyl-cyclobutane-1,3-dione (from Example 4.1) was reacted with benzaldehyde and 5-fluoro-3-methyl-1H-indole to give the title compound as a red solid. MS: 424.5 ([M–H]⁻).

Example 15

N-{2-[(2-Hydroxy-3-methyl-4-oxo-3-p-tolyl-cyclobut-1-enyl)-phenyl-methyl]-1H-indol-3-ylmethyl}-acetamide

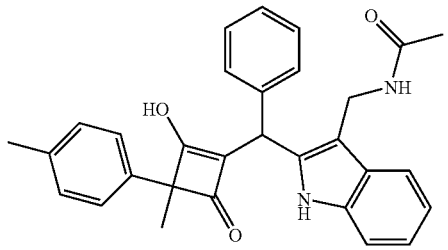

Using general procedure C, 2-methyl-2-p-tolyl-cyclobutane-1,3-dione (from Example 4.1) was reacted with benzaldehyde and N-(1H-indol-3-ylmethyl)-acetamide (Lit. 6) to give the title compound as an off-white solid. MS: 463.4 ([M–H]⁻).

Example 16

N-{6-Chloro-2-[(2-hydroxy-3-methyl-4-oxo-3-p-tolyl-cyclobut-1-enyl)-phenyl-methyl]-1H-indol-3-ylmethyl}-acetamide

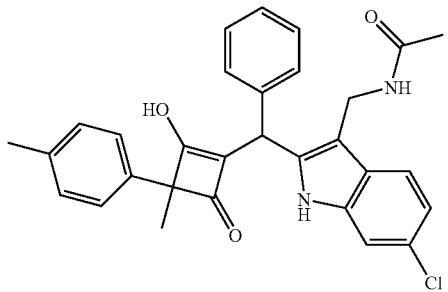

Using general procedure C, 2-methyl-2-p-tolyl-cyclobutane-1,3-dione (from Example 4.1) was reacted with benzaldehyde and N-(6-chloro-1H-indol-3-ylmethyl)-acetamide (prepared from C-(6-chloro-1H-indol-3-yl)-methylamine by acylation according to Example 1.2) to give the title compound as an off-white solid. MS: 497.3 ([M–H]⁻).

Example 17

N-{2-[(2-Hydroxy-3-methyl-4-oxo-3-p-tolyl-cyclobut-1-enyl)-phenyl-methyl]-7-methyl-1H-indol-3-ylmethyl}-acetamide

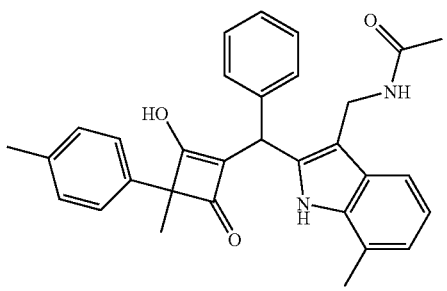

Using general procedure C, 2-methyl-2-p-tolyl-cyclobutane-1,3-dione (from Example 4.1) was reacted with benzaldehyde and N-(7-methyl-1H-indol-3-ylmethyl)-acetamide (prepared from 7-methyl-1H-indole-3-carbaldehyde according to Example 10.1-10.3) to give the title compound as an off-white solid. MS: 477.4 ([M–H]⁻).

Example 18

N-{2-[(2-Hydroxy-3-methyl-4-oxo-3-p-tolyl-cyclobut-1-enyl)-phenyl-methyl]-6-methyl-1H-indol-3-ylmethyl}-acetamide

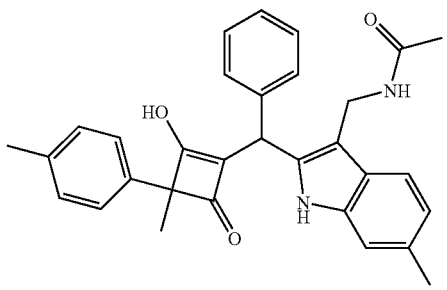

Using general procedure C, 2-methyl-2-p-tolyl-cyclobutane-1,3-dione (from Example 4.1) was reacted with benzaldehyde and N-(6-methyl-1H-indol-3-ylmethyl)-acetamide (from Example 10.3) to give the title compound as a pale red solid. MS: 477.3 ([M–H]⁻).

Example 19

N-{2-[(2-Hydroxy-3-methyl-4-oxo-3-p-tolyl-cyclobut-1-enyl)-phenyl-methyl]-6-methyl-1H-indol-3-ylmethyl}-N-methyl-formamide

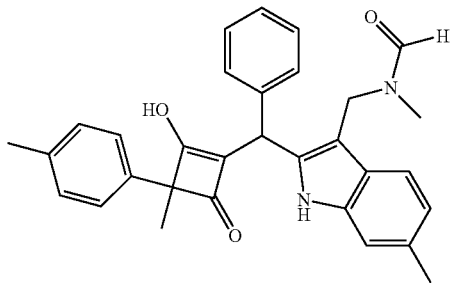

19.1. To a suspension of 6-methyl-1H-indole-3-carbaldehyde (0.96 g, Lit. 5) in methanol (15 ml) was added at 22° C. acetic acid (1.7 ml) and a solution of methylamine in tetrahydrofurane (2 M, 12.0 ml). After stirring for 1 h, sodium cyanoborohydride (0.76 g) was added in 5 portions and stirring was continued for 2 h. The mixture was evaporated and the residue partitioned between aqueous hydrochloric acid (1 N) and dichloromethane. The pH of the aqueous layer was adjusted to 14 using sodium hydroxide followed by extraction with dichloromethane. The organic layer was dried and evaporated to give crude methyl-(6-methyl-1H-indol-3-ylmethyl)-amine.

19.2. To a solution of crude methyl-(6-methyl-1H-indol-3-ylmethyl)-amine (87 mg) in acetonitrile (1 ml) was added diisopropylethyl amine (0.25 ml) and 4-nitrophenyl formate (90 mg) and stirring was continued for 3 h. The mixture was diluted with methanol and acetic acid evaporated and the residue was chromatographed on silica using n-heptane/AcOEt (1:1) to give N-methyl-N-(6-methyl-1H-indol-3-ylmethyl)-formamide as a colorless oil. MS: 202.9 ([M]+).

19.3. Using general procedure C, 2-methyl-2-p-tolyl-cyclobutane-1,3-dione (from Example 4.1) was reacted with benzaldehyde and N-methyl-N-(6-methyl-1H-indol-3-ylmethyl)-formamide to give the title compound as a red solid. MS: 476.6 ([M–H]−).

Example 20

3-Hydroxy-4-methyl-2-(naphthalen-2-yl-phenyl-methyl)-4-phenyl-cyclobut-2-enone

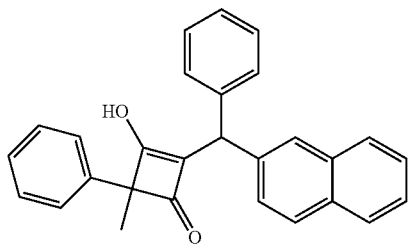

20.1. Using general procedure B, 2-bromonaphthalene was reacted with benzaldehyde to give naphthalen-2-yl-phenyl-methanol as a colorless solid.

20.2. Using general procedure D, 2-methyl-2-phenyl-cyclobutane-1,3-dione (Lit. 1) was reacted with naphthalen-2-yl-phenyl-methanol to give the title compound as a colorless solid. MS: 389.5 ([M–H]−).

Example 21

3-Hydroxy-2-[(6-methoxy-naphthalen-2-yl)-phenyl-methyl]-4-methyl-4-phenyl-cyclobut-2-enone

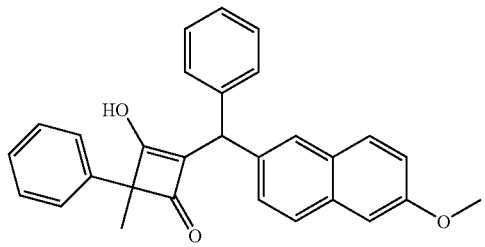

21.1. Using general procedure B, 2-bromo-6-methoxy-naphthalene was reacted with benzaldehyde to give (6-methoxy-naphthalen-2-yl)-phenyl-methanol as a colorless solid.

21.2. Using general procedure D, 2-methyl-2-phenyl-cyclobutane-1,3-dione (Lit. 1) was reacted with (6-methoxy-naphthalen-2-yl)-phenyl-methanol to give the title compound as a colorless solid. MS: 419.3 ([M–H]−).

Example 22

2-(Benzo[b]thiophen-2-yl-phenyl-methyl)-3-hydroxy-4-methyl-4-phenyl-cyclobut-2-enone

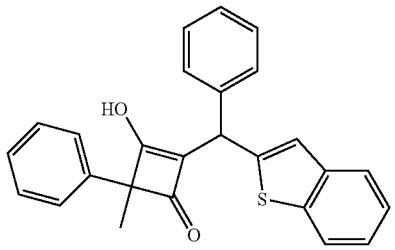

22.1. Using general procedure B, benzo[b]thiophene was reacted with benzaldehyde to give benzo[b]thiophen-2-yl-phenyl-methanol as a colorless solid. MS: 223.1 ([M+H—H$_2$O]+).

22.2. Using general procedure D, 2-methyl-2-phenyl-cyclobutane-1,3-dione (Lit. 1) was reacted with benzo[b]thiophen-2-yl-phenyl-methanol to give the title compound as a colorless solid. MS: 395.3 ([M–H]−).

Example 23

2-[(3,5-Dimethyl-benzo[b]thiophen-2-yl)-phenyl-methyl]-3-hydroxy-4-methyl-4-phenyl-cyclobut-2-enone

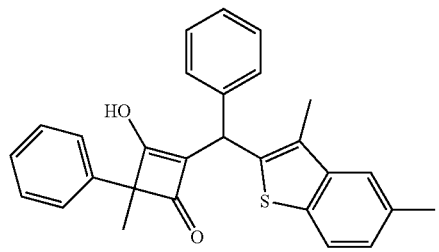

23.1. Using general procedure B, 3,5-dimethyl-benzo[b]thiophene was reacted with benzaldehyde to give (3,5-dimethyl-benzo[b]thiophen-2-yl)-phenyl-methanol as a colorless oil. MS: 251.4 ([M+H—$H_2O$]$^+$).

23.2 Using general procedure D, 2-methyl-2-phenyl-cyclobutane-1,3-dione (Lit. 1) was reacted with (3,5-dimethyl-benzo[b]thiophen-2-yl)-phenyl-methanol to give the title compound as a colorless solid. MS: 423.5 ([M−H]$^−$).

Example 24

3-Hydroxy-4-methyl-2-[(3-methyl-benzo[b]thiophen-2-yl)-phenyl-methyl]-4-phenyl-cyclobut-2-enone

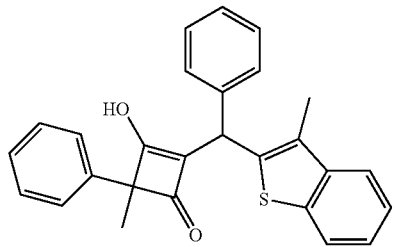

24.1. Using general procedure B, 3-methyl-benzo[b]thiophene was reacted with benzaldehyde to give (3-methyl-benzo[b]thiophen-2-yl)-phenyl-methanol as a pale yellow solid. MS: 236.8 ([M+H—$H_2O$]$^+$).

24.2. Using general procedure D, 2-methyl-2-phenyl-cyclobutane-1,3-dione (Lit. 1) was reacted with (3-methyl-benzo[b]thiophen-2-yl)-phenyl-methanol to give the title compound as a colorless solid. MS: 409.5 ([M−H]$^−$).

Example 25

2-[(5-Fluoro-3-methyl-benzo[b]thiophen-2-yl)-phenyl-methyl]-3-hydroxy-4-methyl-4-phenyl-cyclobut-2-enone

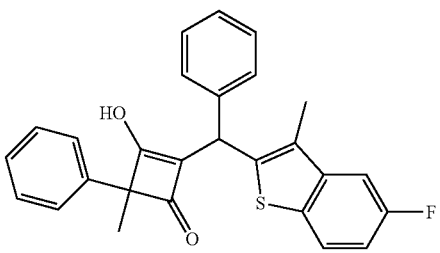

25.1. Using general procedure B, 5-fluoro-3-methyl-benzo[b]thiophene was reacted with benzaldehyde to give (5-fluoro-3-methyl-benzo[b]thiophen-2-yl)-phenyl-methanol as a pale yellow oil. MS: 255.3 ([M+H—$H_2O$]$^+$).

25.1. Using general procedure D, 2-methyl-2-phenyl-cyclobutane-1,3-dione (Lit. 1) was reacted with (5-fluoro-3-methyl-benzo[b]thiophen-2-yl)-phenyl-methanol to give the title compound as a colorless solid. MS: 427.5 ([M−H]$^−$).

Example 26

3-Hydroxy-4-methyl-2-[(5-methyl-benzo[b]thiophen-2-yl)-phenyl-methyl]-4-phenyl-cyclobut-2-enone

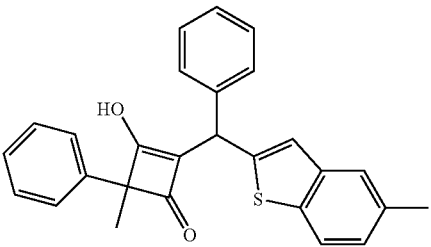

26.1. Using general procedure B, 5-methyl-benzo[b]thiophene was reacted with benzaldehyde to give (5-methyl-benzo[b]thiophen-2-yl)-phenyl-methanol as a colorless solid. MS: 237.1 ([M+H—$H_2O$]$^+$).

26.2. Using general procedure D, 2-methyl-2-phenyl-cyclobutane-1,3-dione (Lit. 1) was reacted with (5-methyl-benzo[b]thiophen-2-yl)-phenyl-methanol to give the title compound as a colorless solid. MS: 409.3 ([M−H]$^−$).

Example 27

3-Hydroxy-4-methyl-2-[(6-methyl-benzo[b]thiophen-2-yl)-phenyl-methyl]-4-phenyl-cyclobut-2-enone

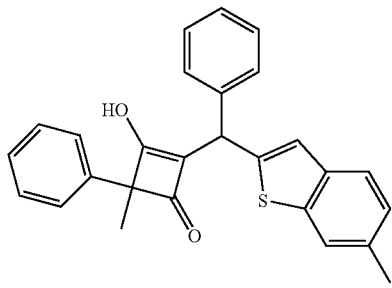

27.1. Using general procedure B, 6-methyl-benzo[b]thiophene was reacted with benzaldehyde to give (6-methyl-benzo[b]thiophen-2-yl)-phenyl-methanol as an off-white solid. MS: 236.9 ($[M+H-H_2O]^+$).

27.2. Using general procedure D, 2-methyl-2-phenyl-cyclobutane-1,3-dione (Lit. 1) was reacted with (6-methyl-benzo[b]thiophen-2-yl)-phenyl-methanol to give the title compound as a pale yellow solid. MS: 409.3 ($[M-H]^-$).

Example A

Film coated tablets containing the following ingredients can be manufactured in a conventional manner:

| Ingredients | Per tablet | |
|---|---|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula I | 3.0 mg |
| Polyethylene Glycol 400 | 150.0 mg |
| Acetic Acid | q.s. ad pH 5.0 |
| Water for injection solutions | Ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula I | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula I | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesiumstearate and the flavouring additives and filled into sachets.

Unless stated to the contrary, all compounds in the examples were prepared and characterized as described. All ranges recited herein encompass all combinations and sub-combinations included within that range limit. All patents and publications cited herein are hereby incorporated by reference in their entirety.

The invention claimed is:

1. A compound of formula I:

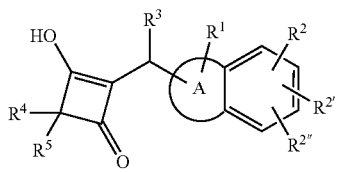

or a pharmaceutically acceptable salt thereof, wherein:
A is a pyrrolyl or thienyl ring;
$R^1$ is selected from the group consisting of:
  (1) hydrogen,
  (2) halogen,
  (3) nitro,
  (4) cyano,
  (5) amino,
  (6) $C_{1-6}$ alkyl,
  (7) heteroalkyl,
  (8) $C_{3-7}$ cycloalkyl,
  (9) $C_{2-6}$ alkenyl,
  (10) $C_{2-6}$ alkynyl,
  (11) hydroxy,
  (12) $C_{1-6}$ alkoxy,
  (13) —NR'R", —($C_{0-6}$ alkylene)-NR'R", in which R' and R" are independently selected from the group consisting of:
    (a) hydrogen,
    (b) $C_{1-6}$ alkyl,
    (c) heteroalkyl,
    (d) formyl,
    (e) $C_{1-6}$ alkylcarbonyl,
    (f) optionally substituted $C_{3-7}$ cycloalkylcarbonyl,
    (g) optionally substituted arylcarbonyl,
    (h) optionally substituted heteroarylcarbonyl,
    (i) optionally substituted heterocyclylcarbonyl,
    (j) $C_{1-6}$ alkylsulfonyl,
    (k) optionally substituted $C_{3-7}$ cycloalkylsulfonyl,
    (l) optionally substituted arylsulfonyl,
    (m) optionally substituted heteroarylsulfonyl and
    (n) optionally substituted heterocyclylsulfonyl,
  (14) —($C_{0-6}$ alkylene)-OR', in which R' is selected from the group consisting of hydrogen, $C_{1-6}$ alkyl, heteroalkyl, formyl and $C_{1-6}$ alkylcarbonyl;
$R^2$, $R^{2'}$ and $R^{2''}$ are independently selected from the group consisting of:
  (1) hydrogen,
  (2) halogen,
  (3) cyano,
  (4) nitro,
  (5) amino,
  (6) mono- or di-$C_{1-6}$ alkyl substituted amino,
  (7) $C_{1-6}$ alkyl,
  (8) $C_{2-6}$ alkenyl,
  (9) $C_{2-6}$ alkynyl,
  (10) heteroalkyl,
  (11) hydroxy, and
  (12) $C_{1-6}$ alkoxy;
$R^3$ is selected from the group consisting of:
  (1) hydrogen,
  (2) halogen,
  (3) cyano,
  (4) nitro,
  (5) amino,
  (6) mono- or di-$C_{1-6}$ alkyl substituted amino,
  (7) $C_{1-6}$ alkyl,
  (8) $C_{2-6}$ alkenyl,
  (9) $C_{2-6}$ alkynyl,
  (10) heteroalkyl,
  (11) hydroxy,
  (12) $C_{1-6}$ alkoxy,
  (13) optionally substituted $C_{3-7}$ cycloalkyl,
  (14) optionally substituted aryl,
  (15) optionally substituted heteroaryl,
  (16) optionally substituted heterocyclyl,
  (17) optionally substituted $C_{3-7}$ cycloalkyl $C_{1-6}$ alkyl,
  (18) optionally substituted aryl $C_{1-6}$ alkyl,
  (19) optionally substituted heteroaryl $C_{1-6}$ alkyl, and
  (20) optionally substituted heterocyclyl $C_{1-6}$ alkyl;
$R^4$ and $R^5$, together with the carbon atom to which they are attached, form an optionally substituted $C_{3-7}$ cycloalkyl ring or an optionally substituted heterocyclyl ring; or alternatively, $R^5$ is hydrogen, halogen or $C_{1-6}$ alkyl, and $R^4$ is selected from the group consisting of:
  (1) hydrogen,
  (2) halogen,
  (3) cyano,
  (4) nitro,
  (5) amino,
  (6) mono- or di-$C_{1-6}$ alkyl substituted amino,
  (7) $C_{1-6}$ alkyl,
  (8) $C_{2-6}$ alkenyl,
  (9) $C_{2-6}$ alkynyl,
  (10) heteroalkyl,
  (11) hydroxy,
  (12) $C_{1-6}$ alkoxy,
  (13) optionally substituted $C_{3-7}$ cycloalkyl,
  (14) optionally substituted aryl,
  (15) optionally substituted heteroaryl,
  (16) optionally substituted heterocyclyl,
  (17) optionally substituted $C_{3-7}$ cycloalkyl $C_{1-6}$ alkyl,
  (18) optionally substituted aryl $C_{1-6}$ alkyl,
  (19) optionally substituted heteroaryl $C_{1-6}$ alkyl, and
  (20) optionally substituted heterocyclyl $C_{1-6}$ alkyl.

2. A compound according to claim 1, wherein:

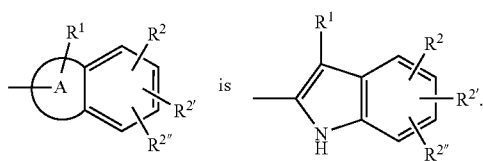

3. A compound according to claim 1, wherein:

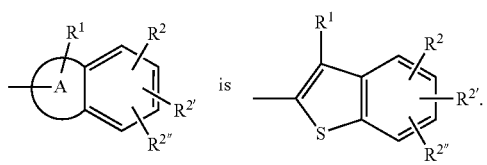

4. A compound according to claim 1, wherein $R^3$ is selected from the group consisting of: (1) $C_{1-6}$ alkyl, (2) optionally substituted aryl, (3) optionally substituted heteroaryl, (4) optionally substituted aryl $C_{1-6}$ alkyl, and (5) optionally substituted heteroaryl $C_{1-6}$ alkyl.

5. A compound according to claim 1, wherein $R^3$ is selected from the group consisting of: (1) $C_{1-6}$ alkyl, (2) phenyl optionally substituted by one to three fluorine atoms, (3) heteroaryl optionally substituted by one to three fluorine atoms, in which the heteroaryl is a monocyclic aromatic radical of 5 or 6 ring atoms, containing one or two ring nitrogen atoms, and (4) phenyl $C_{1-6}$ alkyl.

6. A compound according to claim 1, wherein $R^3$ is phenyl.

7. A compound according claim 1, wherein $R^1$ is selected from the group consisting of: (1) hydrogen, (2) $C_{1-6}$ alkyl, (3) $C_{1-6}$ alkoxy, (4) —($C_{0-6}$ alkylene)-NR'R", in which R' and R" are independently selected from the group consisting of hydrogen, formyl, $C_{1-6}$ alkylcarbonyl, optionally substituted arylcarbonyl, optionally substituted heteroarylcarbonyl, optionally substituted arylsulfonyl and optionally substituted heteroarylsulfonyl, and (5) —($C_{0-6}$ alkylene)-OR', in which R' is hydrogen or $C_{1-6}$ alkylcarbonyl.

8. A compound according to claim 1, wherein $R^1$ is 2-aminoethyl, 2-acetylaminoethyl, 2-(N-formyl-N-methylamino) ethyl, 2-acetylamino-2,2-dimethylethyl, methyl, isopropyl, or 2-hydroxyethyl.

9. A compound according to claim 1, wherein $R^1$ is methyl, 2-acetylaminoethyl, 2-acetylamino-2,2-dimethylethyl, or 2-(N-formyl-N-methylamino)ethyl.

10. A compound according to claim 1, wherein $R^2$, $R^{2'}$ and $R^{2''}$ are independently hydrogen, halogen, $C_{1-6}$ alkyl or $C_{1-6}$ alkoxy.

11. A compound according to claim 1, wherein two of $R^2$, $R^{2'}$ and $R^{2''}$ are hydrogen, and the other is hydrogen, halogen, $C_{1-6}$ alkyl or $C_{1-6}$ alkoxy.

12. A compound according to claim 1, wherein two of $R^2$, $R^{2'}$ and $R^{2''}$ are hydrogen, and the other is hydrogen, chloro, fluoro, methyl, ethyl or methoxy.

13. A compound according to claim 1, wherein two of $R^2$, $R^{2'}$ and $R^{2''}$ are hydrogen, and the other is hydrogen, fluoro or methyl.

14. A compound according to claim 1, wherein $R^4$ and $R^5$, together with the carbon atom to which they are attached, form an optionally substituted $C_{3-7}$ cycloalkyl ring or alternatively $R^5$ is as defined in claim 1 and $R^4$ is selected from the group consisting of: hydrogen, $C_{1-6}$ alkyl, optionally substituted $C_{3-7}$ cycloalkyl, optionally substituted aryl, optionally substituted $C_{3-7}$ cycloalkyl $C_{1-6}$ alkyl, and optionally substituted aryl $C_{1-6}$ alkyl.

15. A compound according to claim 1, wherein $R^5$ is halogen or $C_{1-6}$ alkyl and $R^4$ is selected from the group consisting of (1) $C_{1-6}$ alkyl, (2) optionally substituted aryl, and (3) optionally substituted aryl $C_{1-6}$ alkyl.

16. A compound according to claim 1, wherein $R^4$ is phenyl or 4-methylphenyl; and $R^5$ methyl.

17. A compound selected from the group consisting of:
N-(2-{2-[(2-Hydroxy-3-methyl-4-oxo-3-phenyl-cyclobut-1-enyl)-phenyl-methyl]-6-methyl-1H-indol-3-yl}-1,1-dimethyl-ethyl)-acetamide,
3-Hydroxy-4-methyl-2-[(3-methyl-1H-indol-2-yl)-phenyl-methyl]-4-phenyl-cyclobut-2-enone,
2-[(3,5-Dimethyl-1H-indol-2-yl)-phenyl-methyl]-3-hydroxy-4-methyl-4-phenyl-cyclobut-2-enone,
2-[(3,6-Dimethyl-1H-indol-2-yl)-phenyl-methyl]-3-hydroxy-4-methyl-4-phenyl-cyclobut-2-enone,
2-[(5-Fluoro-3-methyl-1H-indol-2-yl)-phenyl-methyl]-3-hydroxy-4-methyl-4-phenyl-cyclobut-2-enone, and
N-{2-[(2-Hydroxy-3-methyl-4-oxo-3-phenyl-cyclobut-1-enyl)-phenyl-methyl]-6-methyl-1H-indol-3-ylmethyl}-acetamide.

18. A compound selected from the group consisting of:
3-Hydroxy-4-methyl-2-[(3-methyl-1H-indol-2-yl)-phenyl-methyl]-4-p-tolyl-cyclobut-2-enone,
2-[(3,5-Dimethyl-1H-indol-2-yl)-phenyl-methyl]-3-hydroxy-4-methyl-4-p-tolyl-cyclobut-2-enone,
2-[(3,6-Dimethyl-1H-indol-2-yl)-phenyl-methyl]-3-hydroxy-4-methyl-4-p-tolyl-cyclobut-2-enone,
2-[(5-Fluoro-3-methyl-1H-indol-2-yl)-phenyl-methyl]-3-hydroxy-4-methyl-4-p-tolyl-cyclobut-2-enone,
N-{2-[(2-Hydroxy-3-methyl-4-oxo-3-p-tolyl-cyclobut-1-enyl)-phenyl-methyl]-6-methyl-1H-indol-3-ylmethyl}-acetamide, and
N-{2-[(2-Hydroxy-3-methyl-4-oxo-3-p-tolyl-cyclobut-1-enyl)-phenyl-methyl]-6-methyl-1H-indol-3-ylmethyl}-N-methyl-formamide.

19. A pharmaceutical composition comprising a therapeutically effective amount of a compound of claim 1 and a pharmaceutically acceptable carrier or excipient.

* * * * *